United States Patent
Jabri

(10) Patent No.: US 7,783,008 B2
(45) Date of Patent: Aug. 24, 2010

(54) DIGITAL RADIOGRAPH PATIENT POSITIONING SYSTEM AND METHOD

(75) Inventor: Kadri Nizar Jabri, Waukesha, WI (US)

(73) Assignee: General Electric Company, Schenectady, NY (US)

(*) Notice: Subject to any disclaimer, the term of this patent is extended or adjusted under 35 U.S.C. 154(b) by 232 days.

(21) Appl. No.: 11/731,329

(22) Filed: Mar. 30, 2007

(65) Prior Publication Data

US 2008/0240360 A1 Oct. 2, 2008

(51) Int. Cl.
*G01N 23/04* (2006.01)
*H05G 1/64* (2006.01)

(52) U.S. Cl. .................... 378/98.5; 378/62; 378/165

(58) Field of Classification Search ............ 378/20, 378/37, 57, 62, 98.5, 162, 165, 204, 205, 378/210
See application file for complete search history.

(56) References Cited

U.S. PATENT DOCUMENTS

| | | | | |
|---|---|---|---|---|
| 4,953,193 A | * | 8/1990 | Robinson | 378/162 |
| 5,123,040 A | * | 6/1992 | Fabian | 378/182 |
| 6,354,737 B1 | * | 3/2002 | Hufe et al. | 378/205 |
| 7,092,491 B2 | * | 8/2006 | Okoda | 378/162 |
| 7,092,492 B2 | * | 8/2006 | Marn | 378/165 |
| 7,156,553 B2 | * | 1/2007 | Tanaka et al. | 378/205 |
| 7,427,769 B2 | * | 9/2008 | Haug et al. | 250/581 |
| 7,488,108 B2 | * | 2/2009 | Pommi | 378/205 |
| 7,522,701 B2 | * | 4/2009 | Jensen et al. | 378/62 |
| 7,590,221 B2 | * | 9/2009 | Durack | 378/165 |
| 2005/0205813 A1 | * | 9/2005 | Ishikawa | 250/584 |
| 2006/0034427 A1 | * | 2/2006 | Brooks | 378/198 |
| 2008/0130837 A1 | * | 6/2008 | Heath et al. | 378/205 |

* cited by examiner

*Primary Examiner*—Edward J Glick
*Assistant Examiner*—Thomas R Artman
(74) *Attorney, Agent, or Firm*—Fletcher Yoder P.C.

(57) ABSTRACT

A technique is disclosed for placing markers on digital radiographic images, such as projection X-ray and tomosynthesis images. A tag encoding data is disposed on or near a component of a radiographic imaging system, such as on a digital detector. The tag is read during an imaging session, and human readable indicia for the marker is generated that can be permanently included in the resulting images or displayed when desired, such as in an overlay.

28 Claims, 4 Drawing Sheets

DIGITAL RADIOGRAPH PATIENT POSITIONING SYSTEM AND METHOD

BACKGROUND

The present invention relates generally to digital X-ray imaging systems. More particularly, the invention relates to a technique for indicating patient position, image orientation or other indicia on a digital radiograph.

Lead, or more generally, radio-opaque markers are commonly used to indicate patient positioning on radiographs. Such markers have long been used for conventional film-based X-ray systems, and hence have continued to be used for more modem digital systems. Such markers generally are placed in a field of view and may include various indicia, such as letters indicating the orientation of patient anatomies visible in the resulting images (e.g., "L" for left and "R" for right), the anatomies themselves, and so forth. Because the markers are placed in the field of view, their image becomes a permanent part of the X-ray image itself. The indicia may also indicate the image orientation, the identity of a technologist who performed an image session, and so forth.

While they provide a simple and robust indication of patient position or image orientation they are not without drawbacks. For example, with the advent of digital radiography and advanced image processing, the presence of such markers can create artifacts in the image. Lead markers located in the exposure field of view of a tomosynthesis acquisition, for example, can cause significant ripple artifacts that can interfere with diagnostic utility of the resulting images.

In other image marking techniques, some digital radiography systems allow the technologist to define the position of a patient relative to the imaging receptor, using a graphical user interface of a computer workstation. The system then automatically places "digital" laterality markers on the appropriate side of the image. However, the user may still have to place other annotations to indicate patient positioning (e.g., "upright", "supine", etc.), engendering potential problems. Incorrect annotations are possible because the user is often remote from the patient when applying the digital marker or annotation. Furthermore, placing these other annotations introduces change in workflow of multiple types of radiography systems, leading to inefficiencies and potentially to errors. The wide range of digital manipulations available (e.g., flip, rotate 90 degrees, etc.) provide yet another source of human error.

BRIEF DESCRIPTION

The present invention provides a technique for placing markers that are highly detectable on the acquired image, but that avoid problems caused by lead markers in images. While the technique may be used in a wide variety of system types, it is particularly well-suited to digital X-ray systems, X-ray tomosynthesis systems, and so forth. This technique reduces image artifacts caused by lead and other radio-opaque markers, especially in advanced applications of tomosynthesis, and it allows users to remain close to the patient when positioning marks, thereby minimizing the opportunity for errors. Moreover, this present invention allows for a work flow similar to existing X-ray processes for which most current X-ray technologists are trained, and therefore would present little obstacle for adoption from a workflow standpoint.

In accordance with this technique, a patient is positioned as required by factors such as exam type, anatomy to be imaged, clinical condition and so forth. A technologist places a non-lead marker or tag on the image detector, on an appropriate side of the patient. Each marker is configured to indicate its presence, location and identification to the imaging system. Concurrent with generation of the X-ray image, the system detects the presence of the marker, its location, and identity (e.g., content). The system then automatically places the marker "digitally" on the appropriate image by using overlays or annotations, taking into account all image manipulations.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
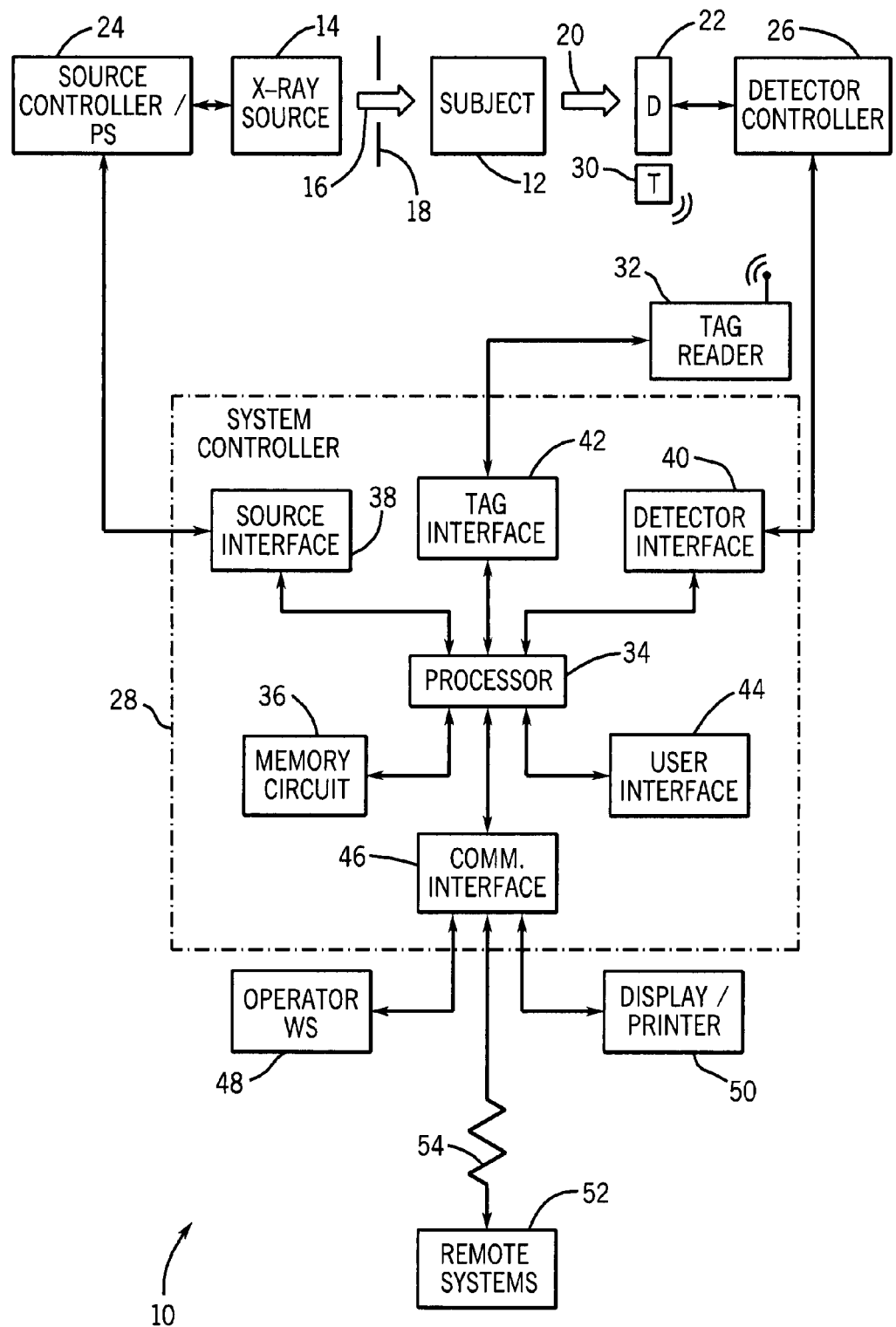
FIG. 1 is a diagrammatical overview of a digital X-ray imaging system in which the present technique is incorporated.

FIG. 1 diagrammatically illustrates an imaging system 10 for acquiring and processing image data to generate radiographic images into which data provided or generated by a marker or tag has been incorporated. In the illustrated embodiment, system 10 is an X-ray imaging system designed to acquire original X-ray image data, incorporate data from a marker or tag, and process the image data for display and analysis in accordance with the present technique. In the embodiment illustrated in FIG. 1, imaging system 10 is designed to create images of a subject 12 by means of X-radiation emitted by a source 14. A stream of radiation 16 passes through a collimator 18 which forms and confines the beam. After passing through the subject, the resulting beam 20 will be altered by attenuation or absorption by tissues within the subject. Beam 20, then, is directed to a digital X-ray detector 22. The foregoing exemplary imaging system may permit various types of alternative positioning of the X-ray source, the beam collimator, and the detector to allow for considerable latitude in selecting a segment of a subject which will be imaged. As described more fully below, detector 22 converts the X-ray photons received on its surface to lower energy photons, and subsequently to electric signals which are acquired and processed to reconstruct an image of the features within the subject.

Although a projection X-ray system is generally represented in FIG. 1, it should be borne in mind that the present technique is not limited to such systems. Indeed, the technique is particularly useful in conjunction with other types and configurations of imaging systems, such as X-ray tomosynthesis systems. As will be appreciated by those skilled in the art, such systems typically rely upon a moving X-ray source, or upon a distributed source, to acquire a series of projection image data sets that can later be used to reconstruct images at different planes through the subject.

Source 24 is controlled by a source controller and power supply 24 which furnishes both power and control signals for examination sequences. Moreover, detector 22 is coupled to a detector controller 26, which commands acquisition of the signals generated in the detector. Detector controller 26 may execute various signal processing and filtration functions, such as for initial adjustment of dynamic ranges, interleaving of digital image data, and so forth. Both source controller and power supply 24 and detector controller 26 are responsive to signals from a system controller 28. In general, system controller 28 commands operation of the imaging system to execute examination protocols and to process acquired image data. In the present context, system controller 28 also includes signal processing circuitry, typically based upon a general purpose or application-specific digital computer, associated memory circuitry for storing programs and routines executed by the computer, as well as configuration parameters and image data, interface circuits, and so forth.

Detector 22 is also coupled to a tag 30, which is a digital marker disposed on the detector. As described more fully below, tag 30 transmits information to a tag reader 32. The system controller 28 acquires (e.g., downloads, reads or otherwise receives) tag data from the tag reader for processing and storage.

In the embodiment illustrated in FIG. 1, the system controller 28 includes a processor 34 designed to coordinate operation of the source and the detector, and to at least partially process acquired image data. The processor may carry out various functionality in accordance with routines stored in a memory circuit 36. The memory circuit may also serve to store configuration parameters, operational logs, raw or processed image data, and so-forth. A source interface 38 cooperates with a processor 34 to output control signals for the source controller and power supply 24, typically to initiate emission of x-ray radiation from the source. The source interface may also collect certain information relating to the behavior and health of the x-ray source. A detector interface 40 cooperates with the detector controller 26. The detector interface may, for example, initiate acquisition of image data, filter or scale image data, or otherwise pre-process the image data to be later handled by the processor 34, such as for image reconstruction and display.

In the embodiment illustrated in FIG. 1, a tag interface 42 cooperates with the tag reader 32 to acquire or download information from the tag 30. The tag interface may receive formatted or raw data from the tag reader 32, and may interpret or decode the tag information, such as to extract tag data which will serve to generate indicia which can be associated with individual images as described more fully below. The tag interface 42 will generally cooperate with the processor 34 for formatting and creating the indicia to be associated with the image file.

The system controller 28 may further include interface circuitry that permits an operator or user to define imaging sequences, determine the operational status and health of system components, and so-forth. Thus, a user interface 44 may be included in the system controller 28. A communication interface 46 will typically also be included that allows for external devices to receive images and image data, and for such external device to command operation of the x-ray system, configure parameters of the system, and so-forth.

In the embodiment illustrated in FIG. 1, system controller 28 may be linked to a range of external devices via the communications interface 46. Such devices may include, for example, an operator workstation 48 for interacting with the X-ray imaging system, processing or reprocessing images, viewing images, and so forth. In the case of tomosynthesis systems, for example, the operator workstation 48 may serve to create or reconstruct image slices of interest at various levels in the subject based upon the acquired image data. Other external devices may include a display or printer as indicated at reference numeral 50. In general, displays, printers, workstations, and similar devices supplied within the system may be local to the data acquisition components, or may be remote from these components, such as elsewhere within an institution or hospital, or in an entirely different location, linked to the image acquisition system via one or more configurable networks, such as the Internet, virtual private networks, and so forth. Such remote systems 52 will typically be linked to the system controller 28 by any one or more of such network links, as indicated generally by reference numeral 54. It should be further noted that the operator workstation 48 may also be coupled to a picture archiving and communications system (PACS). Such a PACS might be coupled to remote clients, such as a radiology department information system or hospital information system, or to an internal or external network, so that others at different locations may gain access to the image and the image data.

Figure 2:
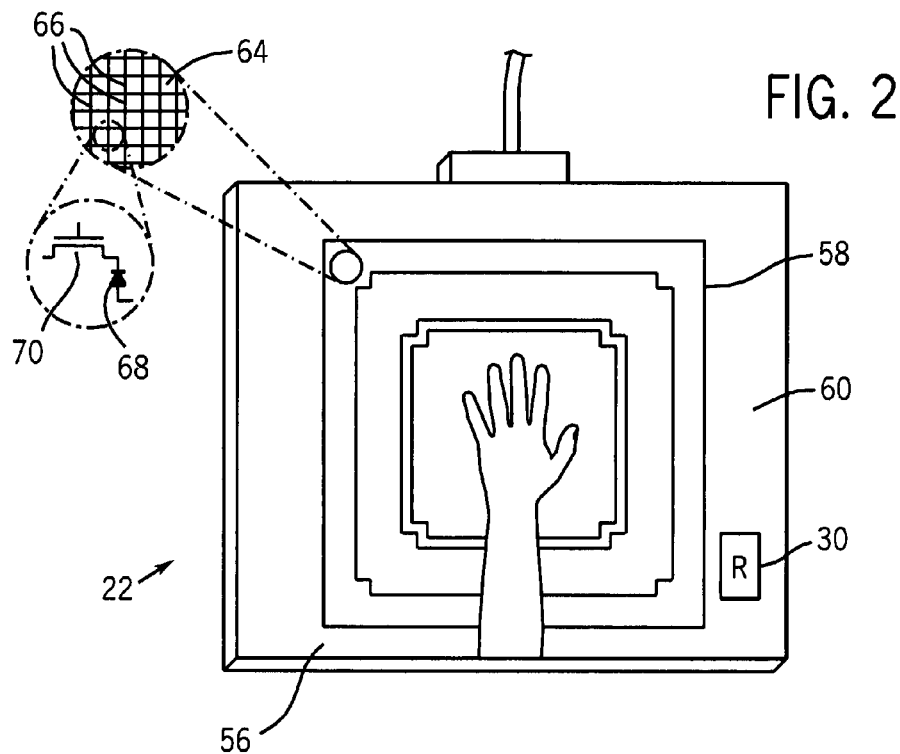
FIG. 2 is a diagrammatical perspective view of an imaging detector and marker or tag, illustrating placement of the marker or tag on the imaging detector.

FIG. 2 is a diagrammatical representation of functional components of digital detector 22. In the illustrated embodiment, tag 30 is a radio frequency identification (RFID) device disposed on the detector 22. Tag 30 is configured to indicate its presence, location (e.g., a particular side, corner or quadrant of the detector), and certain data (e.g., patient orientation, clinician identifying data, etc.) to the tag reader shown in FIG. 1. as will be appreciated by those skilled in the art, detector 22 will typically consist of a scintillator that converts X-ray photons received on the detector surface 56 during examinations to lower energy (light) photons. The surface may be considered to include an image field of view 58 and a region 60 surrounding the field of view. In general, the field of view is the area that will be impacted by radiation and thus create image data. In the illustrated example, the field of view is made up of an array 64 of pixels 66. Each pixel area is associated with a photodiode 68 that converts the light photons to electrical signals (e.g., by charge depletion resulting from the impacting photons), which are representative of the number of photons or the intensity of radiation impacting the individual pixel region of the detector surface. Readout electronics, including transistors 70, recharge the diodes and convert the resulting analog signals to digital values that can be processed, stored, and displayed.

The tag 30 is located outside the field of view, or in the region 60, so as not to interfere with imaging. That is, the tag 30 will not be located in the path of X-ray radiation received by the image data-creating pixel circuitry, and thus will not be part affect the acquired data. In fact, the tag may be provided in any suitable location on any suitable component of the system. However, it is presently contemplated that the tag will most conveniently be physically placed on the detector itself (e.g., in region 60, on an edge of the detector, etc.) as this most closely follows existing and known procedures for using radio-opaque markers.

Figure 3:
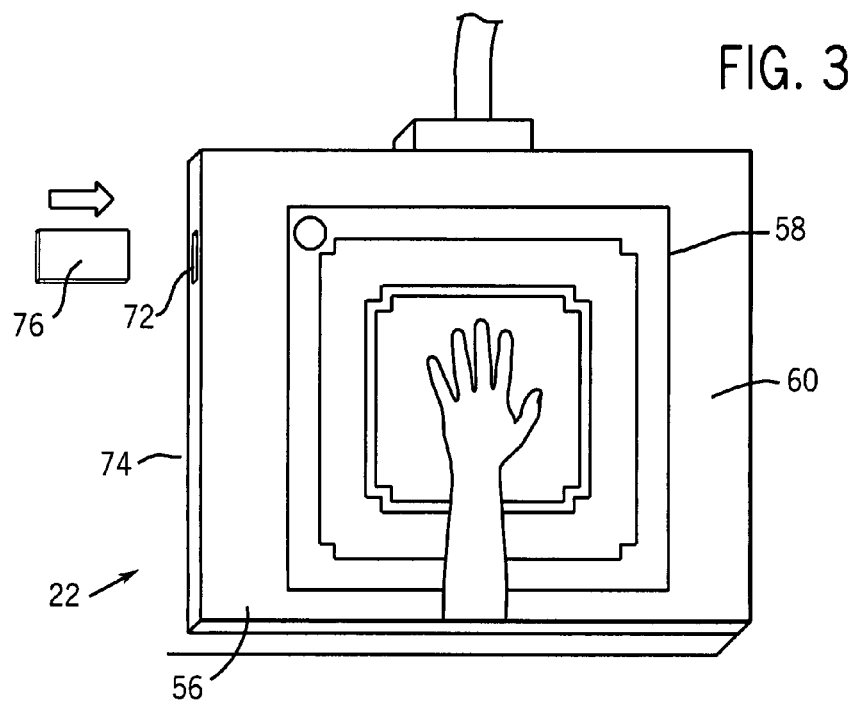
FIG. 3 is a diagrammatical perspective view of an alternative configuration of FIG. 2, where the marker is "plugged" into a receptacle on the side of the imaging detector frame.

Various alternative arrangements may be envisaged in lieu of the RFID tag 30. For example, FIG. 3 illustrates the use of an electronic tag that may include or be programmed to include data that can be read and utilized in a similar manner. In this embodiment, a slot or interface 72 is provided on the detector, such as along an edge 74. An electronic tag 76 may then be inserted into the interface to provide the same information as described above with respect to the RFID tag. Electronic interface circuitry (not shown) within the detector reads the content of the electronic tag and provides the tag data to a tag interface, similar to interface 42 discussed above with reference to FIG. 1. Tag 76 may interface with the detector in accordance with any known standard or protocol, such as universal serial bus (USB) plug-in standard.

It is presently contemplated that various tags, whether RFID, electronic or otherwise, may be pre-configured or programmed, and provided to the radiology clinicians in a set, each labeled with indicia (e.g., writing) that the clinician can read and that corresponds to the indicia encoded in the tag data. The workflow may thus mimic that used for conventional radio-opaque markers. That is, the clinician simply selects the appropriate tag for the examination, and places the tag on or otherwise associates the tag with (e.g., plugs in) the detector. Where desired, more than one tag may be utilized and the tags may be easily changed between images. Where the tags are programmable, a programming unit (not shown) may be associated with the system controller or another device to permit programming of the tag with the desired information.

Figure 4:
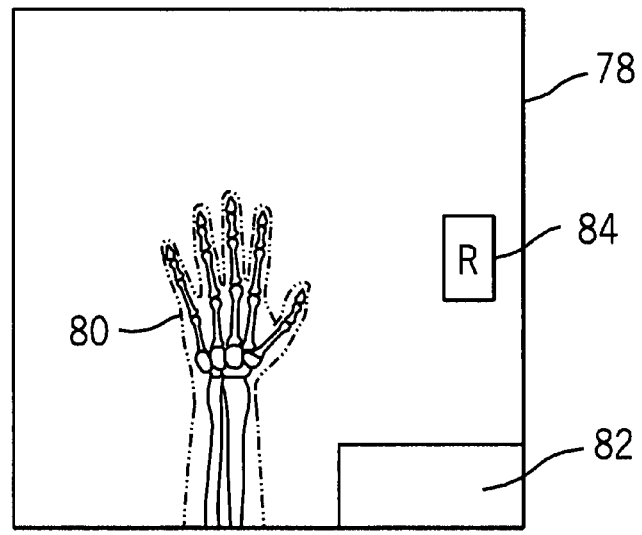
FIG. 4 is an exemplary reconstructed X-ray image incorporating the data obtained from the marker shown in FIG. 2 or 3.

As mentioned above, and as described in greater detail below, the imaging system acquires both image data and the tag data, and can then process both to create an image data file. The file, which may, in fact, include an entire series of images created during an imaging session, is then used to reconstruct and display images of the anatomy of interest. It is on these images that a marker may be displayed or temporarily or even permanently placed to provide indicia of patient position, anatomy, dates, clinician identification, physician identification, patient identification, and so forth. FIG. 4, the illustrated embodiment represents a digital X-ray image 78, portraying a representation of human anatomy 80 (a hand shown in FIGS. 2 and 3) with standard identifying information 82. Disposed within the X-ray image is indicia 84, representing a digital overlay on the X-ray image. In the present exemplary embodiment, indicia 84 may be a DICOM overlay indicating, among other things, patient orientation and tag position on the detector 22.

It should also be noted that the actual physical location of the tags themselves may be detected and the marker (e.g., in a DICOM overlay) may be formed based upon that physical location. That is, the reader, which may in fact include a plurality of readers or sensors, may detect the location of the tag (e.g., by reference to the closest sensor or the strongest signal received by more than one sensor), and this information used to assign the location of the marker that is created for display on the reconstructed image or images.

Figure 5:
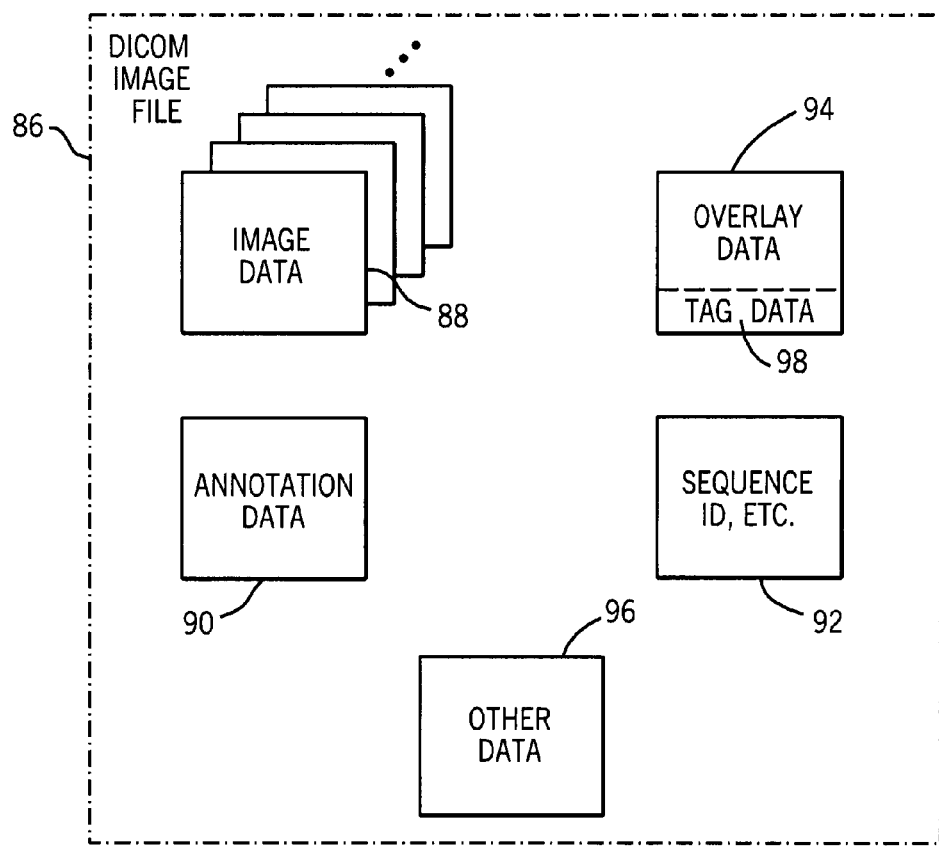
FIG. 5 is a diagrammatical representation of a DICOM image file incorporating marking data acquired from a marker of the invention.

FIG. 5 is illustrates certain of the data components that may be included in a typical DICOM image file 86, including tag data for generating and displaying the desired indicia of patent position and so forth. As will be appreciated by those skilled in the art, the DICOM standards contemplate many different types of data and fields, and the tag data may be included in one such field or data type. In the illustrated embodiment, the DICOM image file consists of image data 88 acquired from the detector during an imaging session. Annotation data 90 may also be included, such as with notes added by a clinician or radiologist. The file will also typically include various identifying information 92, such as for the imaging sequence, the patient identification, the date, and so forth. The DICOM standard also permits creation of overlay data 94 which can be selectively displaced on reconstructed images. Other data 96 may also be included in the file, such as data relating to compression or decompression codes, anatomy imaged, and so forth.

The tag data 98, or code representative of indicia derived from the tag data may be included in any one of these fields or data structures, such as in overlay data 94. Again, overlay data 94, including the tag data 98 will encode human readable indicia is generated from data acquired from the tag during the imaging session. By selecting or adjusting data that the tag stores and transmits, various human readable indicia may be obtained. The present embodiment envisions indicia such as, but not limited to, patient orientation (e.g., left, right, etc.), patient positioning (e.g., upright, supine, etc.), clinician identifiers, such as initials, and so forth.

Figure 6:
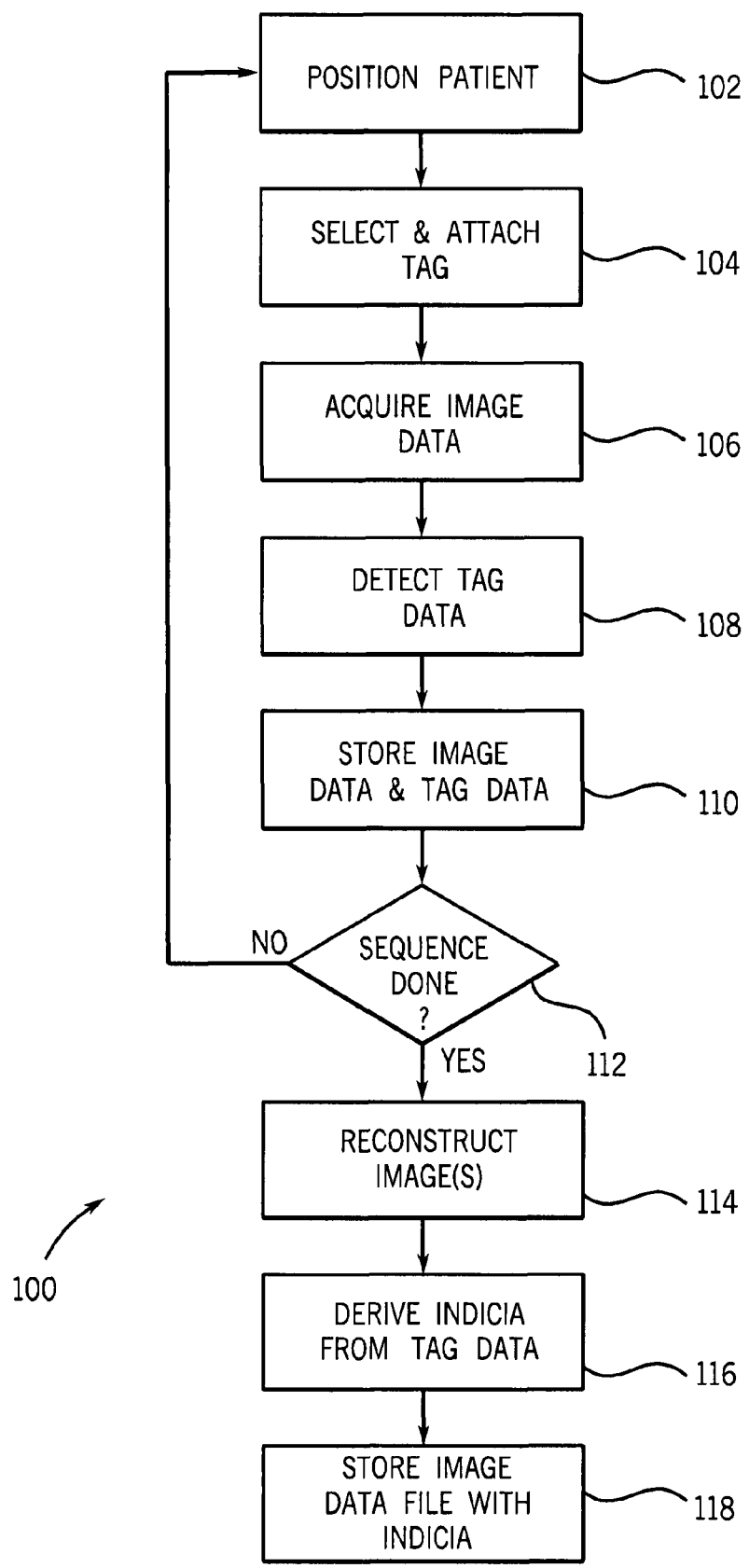
FIG. 6 is a flow chart illustrating exemplary logic in utilizing the present technique to generate a reconstructed X-ray image that incorporates the marker data as an overlay or annotation.

Turning now to FIG. 6, exemplary logic for the workflow involved in implementing the marking or tagging technique of the invention is set forth diagrammatically, and designated generally by the reference numeral 100. The process begins at step 102 with positioning the patient adjacent to or over the detector, with the anatomy of interest in the field of view. At step 104, a tag is selected (or programmed) and attached to the detector (or another component of the system). At step 106, image data is acquired by generating X-ray radiation that passes through the patient anatomy and strikes the digital detector. As noted above, the present system allows for a workflow very similar or even identical to those to which technicians are accustomed. That is, the positioning of the tag, although not generally affecting the data collected by the reader, may be performed much like this is presently done, although the tag will generally not be placed in the field of view of the image. As noted above, where the actual position of the tag can be detected, this physical position may be used to determine where on the reconstructed image or images the marker is ultimately placed. Otherwise, this can be determined by the data encoded by the tag.

At step 108, the tag data is detected as discussed above. Tag and image data from each image acquisition are stored together in a memory component of system controller 28. If further images remain to be acquired, the process may be repeated, as indicated by query block 112. As noted above, the tags used in each image acquisition may be changed, depending upon changes in patient position, anatomy position, detector orientation, and so forth. Upon completion of image acquisition sequence, the system controller reconstructs the digital X-ray images, as indicated at step 114. Finally, human readable indicia are derived from the tag data, as indicated at step 116. The indicia, or data encoding the indicia may then be stored with the image data file, as indicated at step 118 for later display, printing, and so forth.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:
1. A method for indicating patient positioning on a digital X-ray image comprising:
   detecting data from a tag disposed on a component of a digital X-ray imaging system, wherein the tag includes a memory circuit electronically coupled to the component;
   generating digital X-ray image data via the X-ray imaging system; and
   displaying a human readable indicia on an image formed from the image data based upon the detected data from the tag.

2. The method of claim 1, wherein the tag is disposed outside of a field of view of an image defined by the image data.

3. The method of claim 1, wherein the tag includes an RFID device.

4. The method of claim 3, wherein the X-ray imaging system includes an RF reader configured to read data from the RFID device and to provide the data to a processing circuit for determination of the human readable indicia.

5. The method of claim 1, wherein the component includes a digital X-ray detector configured to generate the X-ray image data.

6. The method of claim 1, wherein the human readable indicia include an indication of a patient position in the X-ray imaging system during generation of the image data.

7. The method of claim 1, wherein the human readable indicia is encoded as a DICOM annotation in a data file including processed image data.

8. The method of claim 1, wherein the human readable indicia is encoded as an overlay displayable over a portion of an image reconstructed based upon the image data.

9. The method of claim 1, wherein a location of the tag is detected and a location of the human readable indicia on the image is based upon the detected tag location.

10. The method of claim 1, wherein a location of the human readable indicia on the image is based upon data encoded by the tag.

11. A method for indicating patient positioning on a digital X-ray image comprising:
    detecting data from a tag disposed on a component of a digital X-ray imaging system outside of a field of view of a desired image, the data indicating an orientation of a patient anatomy or a desired orientation of the image;
    generating digital X-ray image data via the X-ray imaging system;
    processing the image data to include a DICOM annotation or overlay of human readable indicia based upon the detected data from the tag, the annotation or overlay identifying at least the patient position during generation of the image data or the desired orientation of the image;
    wherein the tag is one of a set of multiple tags each labeled with human-readable information representative of the data encoded on each respective tag to enable a clinician to select a desired tag from the set of multiple tags and place the desired tag on the component to determine the DICOM annotation or overlay of human readable indicia included with the processed image data.

12. The method of claim 11, wherein the tag includes an RFID device.

13. The method of claim 12, wherein the X-ray imaging system includes an RF reader configured to read data from the RFID device and to provide the data to a processing circuit for determination of the human readable indicia.

14. The method of claim 11, wherein the tag includes a memory circuit electronically coupled to the component.

15. The method of claim 11, wherein the component includes a digital X-ray detector configured to generate the X-ray image data.

16. The method of claim 11, wherein the human readable indicia include at least the patient position during generation of the image data or the desired orientation of the image.

17. The method of claim 11, wherein the human readable indicia is encoded as a DICOM annotation or overlay in a data file including processed image data.

18. The method of claim 11, wherein the DICOM annotation or overlay is displayed over a portion of an image reconstructed based upon the image data.

19. A digital imaging system comprising:
    a tag configured to store data indicating at least an orientation of a patient anatomy or a desired orientation of an image;
    a tag detector for detecting data from the tag during exposure of a digital X-ray detector in an imaging sequence;
    an X-ray imaging system for generating X-ray image data of a subject of interest; and
    processing circuitry for processing the image data and detected tag data into an image file, and for storing the image file.

20. The system of claim 19, wherein the tag is disposed on a component of the imaging system outside of a field of view of an image defined by the image data.

21. The system of claim 20, wherein the component includes a digital X-ray detector configured to generate the X-ray image data.

22. The system of claim 19, wherein the tag includes at least an RFID device or a USB plug-in device.

23. The system of claim 19, wherein the tag detector is coupled to the processing circuitry for transmitting data stored in the tag during an imaging sequence.

24. The system of claim 19, wherein the X-ray imaging system is configured to receive data from the tag detector and to provide the data to the processing circuit by converting the image data into human readable indicia.

25. The system of claim 24, wherein the human readable indicia include at least an indication of an orientation of a patient anatomy or a desired orientation of an image.

26. The system of claim 24, wherein the human readable indicia is encoded as a DICOM annotation in the image file.

27. The system of claim 24, wherein the human readable indicia is encoded as an overlay displayable over a portion of an image reconstructed based upon the image data.

28. A device comprising:
    a machine readable medium;
    computer executable code stored on the medium for processing digital X-ray image data to include human readable indicia based upon data detected during exposure of a digital X-ray detector to X-ray radiation from a tag disposed on a component of a digital X-ray imaging system and disposed outside of a field of view of an image defined by the image data.

* * * * *